(12) United States Patent
Rentoumi et al.

(10) Patent No.: US 11,114,113 B2
(45) Date of Patent: Sep. 7, 2021

(54) MULTILINGUAL SYSTEM FOR EARLY DETECTION OF NEURODEGENERATIVE AND PSYCHIATRIC DISORDERS

(71) Applicant: LangAware, Inc., Athens (GR)

(72) Inventors: Vasiliki Rentoumi, Athens (GR); Georgios Paliouras, Gerakas (GR)

(73) Assignee: LangAware, Inc., Athens (GR)

( * ) Notice: Subject to any disclaimer, the term of this patent is extended or adjusted under 35 U.S.C. 154(b) by 0 days.

(21) Appl. No.: 16/938,266

(22) Filed: Jul. 24, 2020

(65) Prior Publication Data

US 2021/0118465 A1 Apr. 22, 2021

Related U.S. Application Data

(60) Provisional application No. 62/923,364, filed on Oct. 18, 2019.

(51) Int. Cl.
| | |
|---|---|
| *A61B 50/20* | (2016.01) |
| *G10L 25/66* | (2013.01) |
| *G06N 20/00* | (2019.01) |
| *G10L 15/02* | (2006.01) |
| *G10L 15/26* | (2006.01) |
| *G10L 15/22* | (2006.01) |
| *A61B 5/00* | (2006.01) |

(Continued)

(52) U.S. Cl.
CPC ............ *G10L 25/66* (2013.01); *A61B 5/4088* (2013.01); *A61B 5/4803* (2013.01); *A61B 5/7267* (2013.01); *A61B 5/7275* (2013.01); *A61B 5/7475* (2013.01); *G06N 20/00* (2019.01); *G10L 15/02* (2013.01); *G10L 15/063* (2013.01); *G10L 15/22* (2013.01); *G10L 15/26* (2013.01); *G16H 10/60* (2018.01); *G16H 15/00* (2018.01); *G16H 50/20* (2018.01); *G16H 50/30* (2018.01)

(58) Field of Classification Search
CPC ..... A61B 54/4803; G10L 17/26; G10L 25/26; G10L 25/66; G10L 15/02
See application file for complete search history.

(56) References Cited

U.S. PATENT DOCUMENTS 6,157,913 A * 12/2000 Bernstein ................. G09B 7/02
434/169
9,579,056 B2 * 2/2017 Rosenbek ............ A61B 5/7275
(Continued)

OTHER PUBLICATIONS

Extended European Search Report Issued in European Patent Application No. 20187797.4 dated Dec. 16, 2020 (10 pages).
(Continued)

*Primary Examiner* — Daniel Abebe
(74) *Attorney, Agent, or Firm* — Dorsey & Whitney LLP

(57) ABSTRACT

The present disclosure provides a system for predicting a disease state based on speech occurrences. A feature extraction module extracts a plurality of lingual features from a speech record of the speech occurrence. The lingual features are chosen based on a correlation between the lingual features and the disease state in at least a first language and a second language. The lingual features are consistent for transcripts in at least the first language and the second language. A prediction module including a trained classification model generates a prediction of the disease state for speech occurrences in at least the first language and the second language using the lingual features extracted from the speech records.

25 Claims, 6 Drawing Sheets

(51) Int. Cl.
*G16H 50/20* (2018.01)
*G16H 10/60* (2018.01)
*G16H 50/30* (2018.01)
*G16H 15/00* (2018.01)
*G10L 15/06* (2013.01)

(56) References Cited

U.S. PATENT DOCUMENTS

| | | | |
|---|---|---|---|
| 9,747,902 B2* | 8/2017 | Jasinschi | G10L 25/66 |
| 2007/0213982 A1* | 9/2007 | Xi | G10L 15/26 |
| | | | 704/243 |
| 2012/0265024 A1 | 10/2012 | Shrivastav et al. | |
| 2013/0304472 A1* | 11/2013 | Pakhomov | G10L 15/005 |
| | | | 704/254 |
| 2015/0154980 A1* | 6/2015 | Khan | G10L 21/06 |
| | | | 704/203 |
| 2015/0265205 A1* | 9/2015 | Rosenbek | A61B 5/4803 |
| | | | 600/586 |
| 2019/0080804 A1 | 3/2019 | Kim et al. | |
| 2020/0237296 A1* | 7/2020 | Schiff | A61B 5/04842 |

OTHER PUBLICATIONS

Fraser, Kathleen C. et al., "Multilingual Prediction of Alzheimer's Disease Through Domain Adaptation and Concept-Based Language Modelling", Proceedings of the 2019 Conference of the North American Chapter of the Association for Computational Linguistics: Human Language Technologies, vol. 1 (Long and Short Papers), Jun. 2-7, 2019, pp. 3659-3670 (12 pages).

Li, Bai et al., "Detecting Dementia in Mandarin Chinese using Transfer Learning from a Parallel Corpus", arXiv.org, Cornell University Library, 201 Olin Library Cornell University Ithaca, NY 14853, Mar. 3, 2019.

* cited by examiner

MULTILINGUAL SYSTEM FOR EARLY DETECTION OF NEURODEGENERATIVE AND PSYCHIATRIC DISORDERS

BACKGROUND

Alzheimer's disease often presents with changes in spoken language patterns. Early diagnosis based on changes in spoken language patterns may be difficult to identify, making Alzheimer's, and other neurodegenerative diseases difficult to diagnose at the early stages.

SUMMARY

Example methods are described herein. An example method generates a feature vector representing a speech occurrence. The feature vector comprises a plurality of lingual features of speech of the speech occurrence. The lingual features are chosen based on accuracy in determining a disease state and include both word based features derived from analysis of words within the speech and complex features derived from analysis of the speech as a whole. The example method generates a prediction by passing the feature vector as input to a decision module. The decision module comprises a machine learning model trained using data regarding disease state. The example method returns the prediction to one or more user devices.

In an example method, the word based lingual features may include at least one unigram feature indicating a recurrence of a word in the speech.

In an example method, the complex lingual features may include at least one acoustic feature extracted from an audio recording of the speech.

In an example method, returning the prediction to the one or more user device may comprise returning context information with the prediction.

In an example method, the context information may include at least one of the lingual features of the transcript and patient performance history.

In an example method, the feature vector may be generated by extracting one or more lingual features from an audio recording of the speech and extracting one or more of the lingual features from a transcript of the speech.

An example method described herein extracts features of speech from one or more datasets including speech records in a first language and speech records in a second language, where the one or more datasets include speech records and a known outcome corresponding to each of the speech records. The method further identifies a subset of the extracted features for accurately predicting a disease state or risk factor for speech records in both the first language and the second language. To identify the subset of extracted features, the method trains a plurality of models using different experimental subsets of features to predict the disease state for each of the speech records, assesses an accuracy of the plurality of models by comparing the predicted disease state to the known outcome for each of the speech records, and identifies the experimental subset of features used to train one or more models based on the assessed accuracy.

In an example method, the extracted features may include both word based features derived from analysis of words within the speech and complex features derived from analysis of the speech as a whole.

In an example method, each of the experimental subsets of features may include at least one unique word based feature of the word based features.

An example method may identify a most accurate model of the plurality of models based on the assessed accuracy of the plurality of models and may designate the experimental subset of features used to train the most accurate model as the subset of features for accurately determining a disease state for transcripts in both the first language and the second language.

An example method may configure a system for cross-lingual diagnosis by identifying a most accurate model of the plurality of models based on the assessed accuracy of the plurality of models, configuring a second feature extraction module to extract the experimental subset of features used to train the most accurate model from speech records in the first language and the second language, and configuring a prediction module including the most accurate model.

In an example method, the speech records may include recorded audio of speech and written transcripts of speech.

In an example method, the plurality of models may be random forest classifiers.

Example systems are described herein. An example system for predicting a disease state based on a speech occurrence includes a feature extraction module configured to extract a plurality of lingual features from speech of the speech occurrence, where the plurality of lingual features include both word based features and complex features. Word based features comprise features derived from analysis of words within the speech and complex features comprise features derived from analysis of the speech as a whole. The example system includes a prediction module including a trained classification model, wherein the trained classification model is trained to generate a prediction of the disease state for a patient based on the speech using the plurality of lingual features extracted from the speech. A communication interface is configured to return the prediction of the disease state and one or more analytics regarding the speech and the lingual features to a user device for display to a user.

In an example system, the word based features may include one or more unigram features indicating a recurrence of a word in the speech.

In an example system, the plurality of lingual features may be experimentally determined to have high predictive value of the disease state for speech in each of a first language and a second language.

In an example system, experimentally determining high predictive value of the plurality of lingual features may occur while training the trained classification model.

In an example system, the complex features may include at least one acoustic feature extracted from an audio recording of the speech.

In an example system, the analytics returned by the communication interface may include patient scores in predetermined linguistic categories, where the plurality of lingual features correlate to one of the predetermined linguistic categories.

In an example system, the communicate interface may be further configured to receive a final diagnosis from a user device, where the final diagnosis is communicated to the prediction module to refine the trained classification model.

Additional embodiments and features are set forth in part in the description that follows, and will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure. One of skill in the art will understand that each of the various aspects and features of the disclosure may advantageously be used separately in some instances, or in combination with other aspects and features of the disclosure in other instances.

BRIEF DESCRIPTION OF THE DRAWINGS

The description will be more fully understood with reference to the following figures in which components are not drawn to scale, which are presented as various examples of the present disclosure and should not be construed as a complete recitation of the scope of the disclosure, characterized in that.

DETAILED DESCRIPTION

Figure 1:
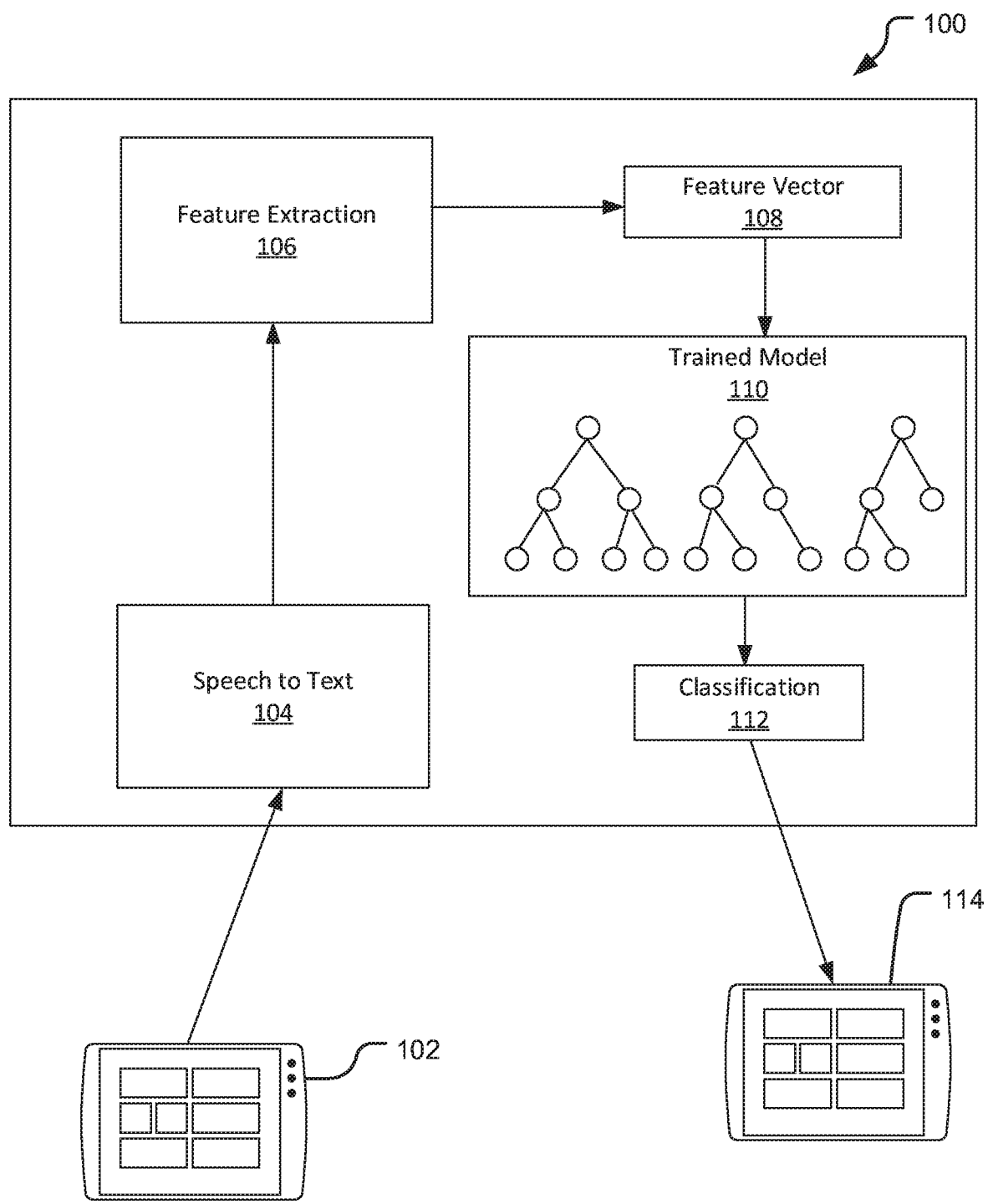
FIG. 1 is a schematic diagram of an example diagnosis decision support system.

According to the present disclosure, a system for early detection of Alzheimer's disease is provided. The system generates a prediction of whether a patient has Alzheimer's disease, another form of dementia, or other neurodegenerative disease based on an occurrence of speech, such as the patient's speech in response to a task or free form speech. For example, the patient may be shown a picture and asked to describe the picture, be asked to retell a popular short story or fairy tale, or be asked to describe how to perform a specific task. The patient's speech is recorded and a transcript is generated of the speech for analysis. The transcript may be generated using available speech to text applications or, in some implementations, may be generated by hand.

The speech transcript is fed into a feature extraction module and a predictive module to generate a prediction of disease state (e.g., whether the patient has a neurodegenerative disease) or predicted risk factor for developing cognitive decline. In some implementations, the speech recording may also be provided to the feature extraction module. In some implementations, other types of speech records, such as video or images, may be provided to the feature extraction module. The feature extraction module analyzes the transcript to determine values for different complex and simple features of narrative competence pertaining to language and speech. Simple features may belong to the purely lexical domain such various ranges of n-grams (unigrams, bigrams). Complex features may belong and are not limited to the lexical and syntactic competence domain, to the semantic/conceptual domain (e.g., semantic coherence, cohesion, specificity), to the socio/pragmatics domain, to the phonological, speech and acoustics and to the extralinguistics domain. Additionally, features from the pshycholinguistic and the affective domain (i.e. emotions and sentiments) may be included. All the above feature domains yield a high predictive value of neurodegenerative diseases. The values are then passed to the predictive module to generate the disease state prediction. The predictive model may be a machine learning based model trained to predict disease state based on a subset of extracted features.

Once the predictive model generates a prediction, the prediction may be returned to a physician, the patient, the patient's caregiver, or other person involved in treatment and diagnosis of the patient. The returned prediction may include analytics regarding the different feature domains used to generate the prediction along with a likelihood, confidence interval, or other measure of likely accuracy of the prediction. For example, in one implementation, the prediction may include an indication that there is an 80% chance that the patient has or will be diagnosed with Alzheimer's based on deficits in lexical and syntactic competence and socio/pragmatics domains.

Generally, speech from a patient with Alzheimer's, dementia, or other neurodegenerative disease will have different characteristics than speech from a patient without a neurodegenerative disease. For example, patients with neurodegenerative diseases may have a more limited vocabulary, an increased use of pronouns in place of nouns, use more generic terms, and have a higher instance of disfluencies, among other features. Speech features that are strongly correlated to neurodegenerative disease may vary across languages. For example, native speakers of a first language with neurodegenerative disease may employ words with different frequency, over the native speakers of a second language with neurodegenerative disease. Accordingly, a model developed to generate predictions for transcripts in the first language may be unreliable in generating predictions for transcripts in the second language, when it is solely based on word level information. However, having a model that can accurately diagnose patients speaking distinct languages is often helpful in clinical settings.

In some implementations, a multilingual diagnosis system may include predictive models for a variety of languages, such that the multilingual diagnosis system is able to generate predictions for multiple languages. In some implementations, a cross-lingual model may be generated and used within the system, where one predictive model is generated for more than one language.

To generate a cross-lingual model (a model that can predict disease state in more than one language), the model is trained using speech records (e.g., recordings or transcripts) in multiple languages. Part of the training process includes choosing a subset of linguistic features that are predictive of disease state for each of the languages included in the model. Once the cross-lingual set of features is identified and extracted, the model can be trained using the extracted features as vectors representing the speech records with known outcomes (e.g., labeled observations) in both languages before being deployed in the clinical system for patient diagnosis. In some implementations, single language models that form a multilingual diagnosis system may be trained or generating using, in part, a cross-lingual model or the features identified in the generation of a cross-lingual model.

Systems including different models can be trained and implemented in clinical settings where certain language combinations are desired. For example, a model including both English and Spanish options may be used in the United States while a model including English and French options may be used in Canada. Other combinations of languages, such as a model including English and Greek options, may be created or used in additional settings. In implementation, the system may include a cross-lingual model (where one model is able to generate predictions for more than one language) and/or multiple single language models forming a multilingual system.

FIG. 1 is a high level diagram showing implementation of the multi-lingual and cross-lingual diagnosis system. Generally, a patient uses a patient device 102 to interact with the multi-lingual diagnosis system. The patient device 102 may include a display, a user interface such as a touch screen, a microphone to collect speech, and a network interface. The multi-lingual diagnosis system prompts the patient to speak, generally via the display of the patient device 102. For example, the display of the patient device 102 may display a picture with instructions for the patient to describe what it shown in the picture. In other implementations, the display of the patient device 102 may display instructions prompting the patient to retell a popular story or to narrate a common procedure (such as making breakfast or packing for a vacation). Further, instructions may be displayed for performing a verbal fluency test, a verbal memory test, or other cognition based test. In some implementations, instructions may be relayed to the patient via speakers, headphones, tactile output, or other methods of relaying communications to a patient.

The patient generates some speech in response to the prompt of the system. In one implementation, the speech is recorded using a microphone integrated in the patient device 102 (or otherwise connected thereto). A microphone may also be communicatively attached to the patient device 102 through a data port of the patient device 102 or through a wireless (e.g., Bluetooth or WiFi) connection. Once the speech is recorded using the patient device 102 (or another device connected to the patient device), the speech may be conveyed to a speech to text module 104 to generate a text transcript of the speech. In some implementations, the speech to text module 104 may be executed by the patient device 102. In other implementations, the speech to text module 104 may be part of a remote system (e.g., a cloud computing system or prediction system server) accessible by the patient device 102. Where the speech to text module 104 is not executed by the patient device 102, the patient device 102 sends the speech to the remote speech to text module for conversion to a text file. In some implementations, speech to text functions may be performed manually and the speech may be sent electronically to personnel responsible for generating a speech transcript.

The speech to text module 104 sends the text file transcript to a feature extraction module 106 that extracts features from the text transcript to generate a feature vector. Elements of the feature vector are generally a numeric representation of a linguistic feature in the transcript, such as a ratio of the number of pronouns used in the transcript to the number of nouns used in the transcript or the number of times a word or idea is included in the transcript. Linguistic features included in the feature vector are chosen based on their predictive value for all languages in the cross-lingual model. For multi-lingual systems, features may be included based on the predictive value for each language in the multilingual model. The features are generally determined during the training stages of the model, as described in more detail with respect to FIG. 2.

The feature extraction module 106 may extract both simple features and complex features from the text transcript. Simple features (e.g., purely lexical or word based features) are generally unigram features representing the (possibly scaled) number of times a word appears within a transcript. The feature extraction module 106 may lemmatize some words in the transcript so that words representing the same or similar concepts are counted together. For example, the words "flower" and "flowers" may be viewed as the same unigram for purposes of the simple feature. In some implementations, the feature extraction module 106 will look for specific unigrams, or ranges of n-grams (i.e. bigrams, thrigrams etc.) in the transcript that have been shown to be predictive for a given task and group of languages. In other implementations, the feature extraction module 106 automatically generates a representation for each unigram in the transcript.

Complex features are generally measurements for lexical complexity using, for example, the number of instances of certain parts of speech over the transcript as a whole. Other complex features may include mean sentence length, word repetition, and variety of words in the transcript. When an audio input is provided as part of the speech record, other complex features, such as acoustics or inflection, may also be extracted from the speech record. Accordingly, complex features are extracted through analysis of a transcript, audio recording, or both as a whole. To extract complex features from the transcript, the feature extraction module 106 may include or communicate with additional resources, such as part of speech taggers, to classify individual words in the transcript. The feature extraction module 106 will generally have access to additional resources in each language included in the prediction system. The feature extraction module 106 represents the extracted simple features and complex features in a feature vector 108.

The feature vector 108 is used as input for a trained model 110 to generate a classification 112 for the transcript represented by the feature vector 108. The trained model 110 is generally trained to classify transcripts in two or more languages in response to an occurrence of patient speech (e.g., a patient describing a picture). The trained model 110 is generally trained using transcripts with known classifications in each language included in the prediction system (labeled observations). As described in more detail below with respect to FIG. 2, the trained model 110 may be trained as part of the feature selection process. In the described implementation, the trained model 110 is a random forest, including multiple decision trees that each classify the transcript individually. The classification of the random forest is generated based on consensus of the multiple decision trees that comprise the random forest. In other implementations, the trained model 110 may use another classifier, such as a naïve Bayes classifier, a support vector machine, or a single decision tree. Further, the trained model 110 may be implemented using a deep learning approach, such as a cognitive neural network.

The classification 112 of the trained model 110 is returned to a physician device 114. The physician device 114 may be any type of computing device. In some implementations, the physician device 114 and the patient device 102 are the same device. In other implementations, the classification 112 of the trained model may be returned to the physician device 114, the patient device 102, and may be available to other devices through, for example, a patient's electronic medical records. The classification 112 may include additional information to assist the physician, patient, and other interested parties in understanding how the prediction system generated the classification 112. For example, the classification 112 may be returned with feature scores reflecting, the patient's lexical complexity or use of speech disfluencies. In some implementations, the system may be used for the same patient at regular intervals (e.g., every three months) and the patient's feature scores may be tracked to indicate if the patient is stable or is deteriorating. To provide a physician or other provider with more data, the system may include remote monitoring to assess cognitive status at pre-specified intervals. The cognitive scores gathered over time may assist healthcare professionals in making more informed decisions about individual patients and to prioritize between patients.

In some implementations, a risk factor assessment may be returned to the physician device 114. Where a risk factor assessment is returned to the physician device, free speech input (apart from the speech given in response to a task) from the patient may also be used as an input to the model.

In some implementations, the physician device 114 and the patient device 102 may be remote from each other, so that the prediction system may be used by a patient before an initial appointment and the physician may review the patient's results before the appointment. The physician device 114 may be connected to a network or patient records repository and the physician may send the classification 112 and accompanying information to a patient's electronic medical record. In some implementations, the physician device 114 (or another device used in a clinical setting) may return a diagnosis to the prediction system to increase accuracy of the trained model 110 over time. For example, the physician may order additional testing for a patient based on the patient's classification 112 and determine that the patient does not have a neurodegenerative disease. That result may then be returned to the system as additional training for the trained model 110. This may be helpful for increasing the accuracy of the trained model 110 in clinical settings where, for example, average patients have less formal education than patients whose data was used to train the trained model 110. In these cases, refining the trained model 110 by giving feedback on a specific clinical population may increase the accuracy of the trained model 110 for that patient population.

In further implementations, the trained model 110 may be periodically updated to, for example, add additional languages to the cross-lingual diagnosis system or to implement new speaking tasks. Training of an updated trained model may occur in the same manner as training the original trained model 110.

Figure 2:
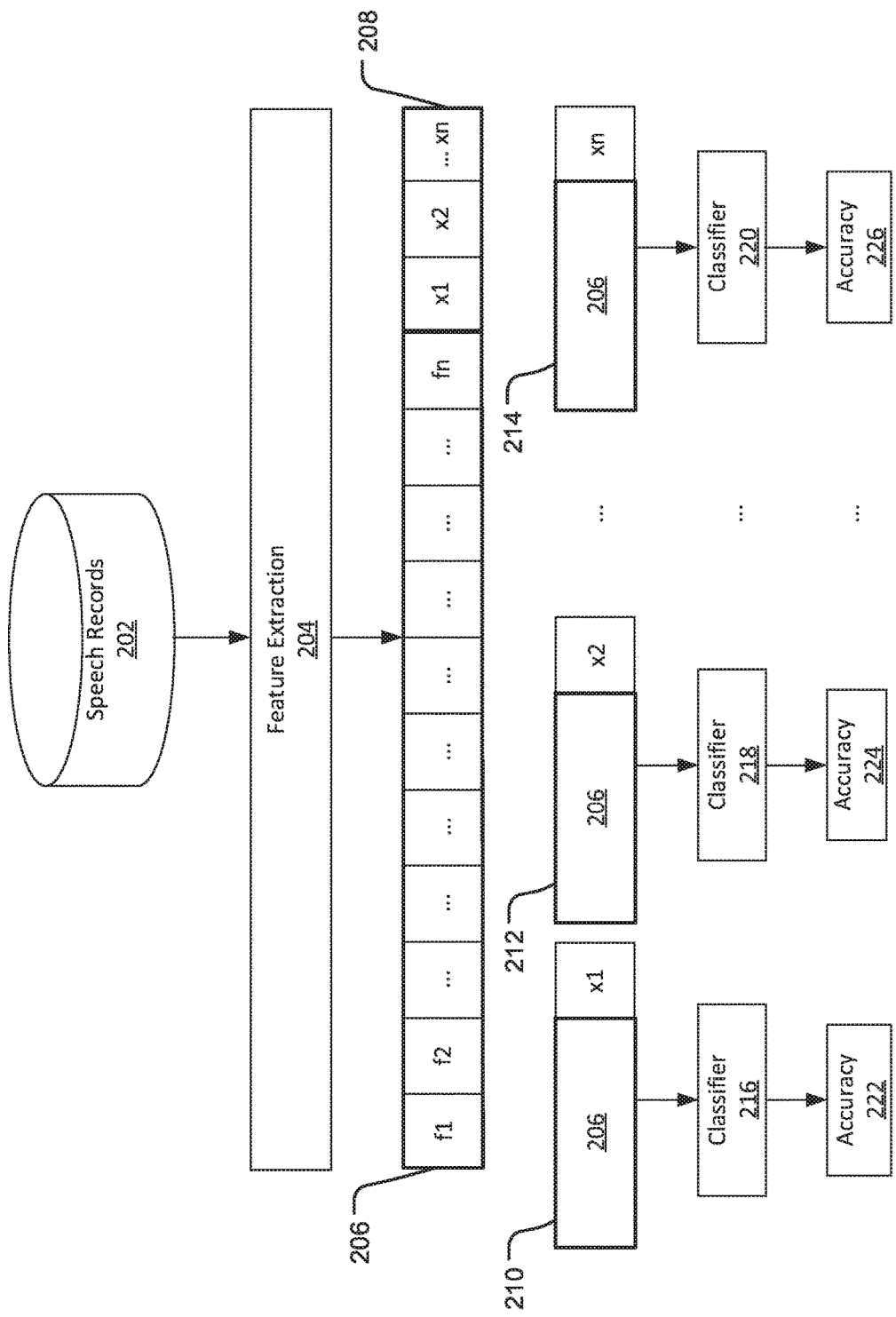
FIG. 2 is a diagram illustrating feature selection and training of a random forest classifier for use as a predictive model in a diagnosis decision support system.

FIG. 2 is a diagram illustrating feature selection and training of a random forest classifier for use as a predictive model in a cross-lingual diagnosis system. Speech records 202 are stored and accessible by a feature extraction module 204 and training of a random forest classifier. The speech records 202 are generally records of speech occurrences in each language to be included in the cross-lingual diagnosis system. The speech records 202 may be collected responsive to a speech task or may be free speech from patients. In some implementations, speech records 202 may include both speech occurrences responsive to tasks and free speech. The responses may be in the form of audio recordings or text transcripts. In some implementations, one speech record includes an audio recording and a text transcript of the audio recording. The speech records 202 may be associated with a known classification (e.g., a neurodegenerative diagnosis or a healthy patient) and may be used as either labeled observations for training a model or unlabeled observations (where labels are hidden from the classifier) for assessing the accuracy of a trained model.

The feature extraction module 204 extracts a complete feature vector 206 from the speech records 202. The feature vector 206 is populated by values corresponding to features of the transcript, such as, lingual features with correlation to a neurodegenerative disease in one or more languages. Features may include, for example, lexical features, that are word types and their frequency related values, complex linguistic features related to, for example, syntactic complexity, lexical variation, or morphosyntactic errors, or the like.

The feature extraction module 204 generally identifies two types of features from the speech records 202. Simple features, or bag of word features, are generally represented as simple scores generated based on term frequencies. For example, the bag of words features may be represented as a frequency vector 208 with a length equal to the vocabulary of a dataset (e.g., the number of distinct words in a dataset), where each value in the frequency vector 208 is the number of times a specific word occurs within a given transcript. In some implementations, the features from vector 208 may be scaled by the length of the document, as well as by the log of their inverse document frequency to reflect how distinctive a word is for a transcript given the collection of transcripts.

Complex features represent more complex metrics measuring, for example, the lexical/grammatical or syntactic complexity of the transcripts. The feature extraction module 204 may use several preprocessing stages to process the transcripts before extracting complex features. For example, in some implementations, the feature extraction module 204 includes language dependent taggers that identify, for example, various parts of speech within the transcripts. Once parts of speech are identified, the feature extraction module 204 can extract complex features such as pronoun to noun ratio, pronoun/noun to word ratio, and numbers of lexical concepts. The feature extraction module 204 may also extract complex features such as mean length of sentences, repeated words, probability of word reuse, and number of grammatical errors for each transcript. The complex features are represented in a complex feature vector 206.

After generating the complex feature vector 206 and the frequency vector 208 for each of the speech records 202, significant features are selected for use in training and implementing a final cross-lingual model. Significant features may vary across language combinations and speech prompts and are generally a subset features of the complete feature vector 206 with a high predictive value for a given combination of languages and a given task. Several methods may be used to select significant features, including, for example and without limitation, forward feature selection (FFS), recursive feature elimination (RFE) and using a machine learning model. FFS uses a predefined subset of the complex feature vector as a base and iteratively evaluates the effect of adding significant simple features to a final feature vector.

In one implementation, FFS uses a random forest model and cross validation to measure the simple features that increase the accuracy of the model and should be included in the cross-lingual diagnosis system. Generally, the random forest includes multiple decision trees and given a data point, a decision tree pushes the data point from its root to one of its leaves, interrogating a single feature value at each step. The leaves of the tree eventually characterize a sample as a member of one of two groups. During a training procedure, the optimal splits are determined and during a prediction task the new, unknown data sample traverses the tree and is directed to a leaf node that will assign a corresponding predicted label. A random forest includes multiple decision trees where for new data points the final decision is made using voting between the individual trees (e.g., the individual trees in the forest reach a consensus on the classification of a transcript). The algorithm introduces an element of randomness due to the fact that the decision trees have access to a different subset of features and a different subset of a dataset as training points.

In FFS, the speech records 202 are randomly split into a number of different groups for training and cross-validation. In many embodiments, the random split means that each training and validation group includes transcripts from each language included in the prediction system. For example, the transcripts may be split into ten different groups with nine groups acting as labeled observations (to train the classifiers) and one group acting as an unlabeled test group to determine the accuracy of the classifiers. The classifiers may be trained using one of the nine groups of labeled observations and tested using the group of unlabeled observations to obtain an accuracy score. A final accuracy score may average the accuracy scores across the nine training groups. Subsets of features, may also be randomly determined for each tree within the random forest such that each tree within the forest returns a classification based on a different subset of features. Each tree within the random forest returns a classification and the final classification of the random forest is determined by consensus of the individual trees.

During FFS, the complex feature vector is augmented by the addition of a single simple feature from the simple feature vector. The augmented feature vector is then evaluated by training the classifier using the augmented features for a number of sets of labeled observations and testing the accuracy the classifier using the augmented features of the unlabeled observations and cross-validating the classifiers. The procedure is repeated for each of the simple features in the simple feature vector and the simple feature producing the classifier with the highest accuracy is added to the final feature vector. The process continues iteratively until the addition of another simple feature for the final feature vector no longer produces a model with a higher overall accuracy. The random forest trained using the final feature vector (e.g., the most accurate classifier) may then be implemented in the prediction system.

FIG. 2 illustrates one simplified iteration of FFS. Speech records 202 are input into the feature extraction module 204, which generates a complex feature vector 206 and a frequency vector 208 of simple features x1, x2, through xn. Augmented vectors 210, 212, and 214 are formed by adding x1, x2, and xn, respectively, to the complex vector. The classifiers 216, 218, and 220 are trained and evaluated using the cross validation methods discussed above for the augmented vectors 210, 212, and 214, respectively. Accuracies 222, 224, and 226 are generated through cross-validation for the classifiers 216, 218, and 220. The classifier corresponding to the highest accuracy may then be the baseline classifier and the corresponding augmented vector may become the base feature vector for the next iteration of FFS. For example, if accuracy 224 was the highest accuracy, then x2 is added to the feature vector. In the next iteration, all remaining simple features would be added individually to the vector including the complex feature vector 206 and x2. If the highest accuracy returned by trained classifiers in the next iteration was not higher than accuracy 224, then the process would end and the final feature vector would consist of the complex feature vector 206 and x2. The classifier 218 would then be included as the trained model (e.g., trained model 110) in the cross-lingual analysis system.

In some implementations, FFS may include reduction of the set of complex features in a similar manner, where the final feature vector is iteratively built from all available features. The complex features may be combined with simple features for FFS, where the most accurate features are added to the final feature vector from the full set until additional features no longer improve accuracy of the classifier. In other implementations, the complex features are selected using a first FFS selection and simple features are then added using a second FFS until the classifier is no longer improved by additional features. Additional approaches may be used, such as RFS. Using RFS, the entirety of the feature set is provided to the classifier. Individual features are removed and the reduced set is provided to the classifier. As features are removed, the impact of removal of features from the set on the classifier's performance is tracked. The least impactful feature is then removed and the procedure is repeated, recursively, until a final subset has been formed. Other feature selection methods may be used in various implementations.

Though the machine learning model is described as a random forest classifier, in other implementations, other types of classifiers, such as support vector machine, naïve Bayes classifiers, and simple decision trees may be used. Additionally, other methods of selecting features for inclusion in a feature vector, including use of a full feature vector, may be used.

Figure 3:
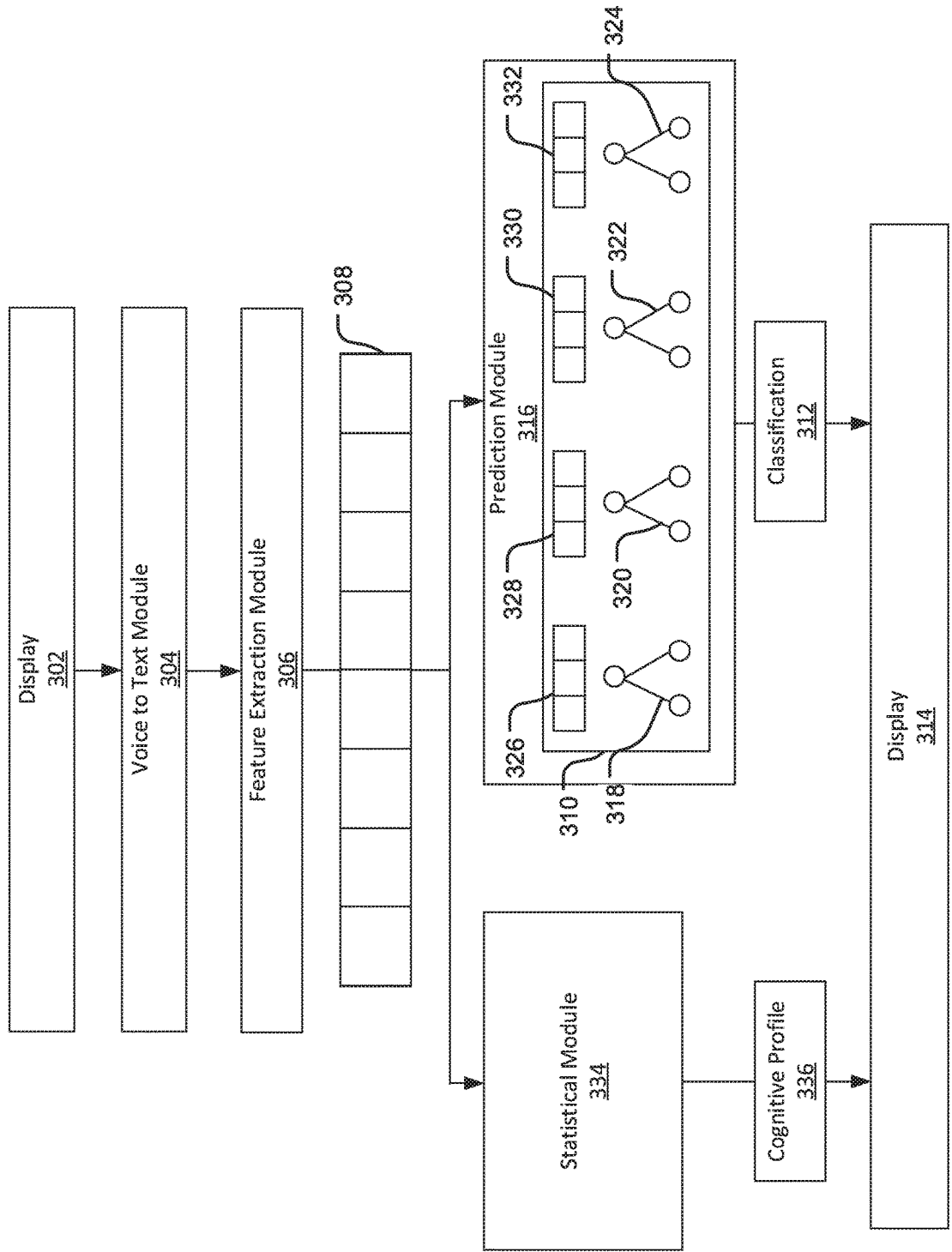
FIG. 3 is a schematic diagram showing a diagnosis decision support system.

FIG. 3 is a schematic diagram showing a cross-lingual diagnosis system. The cross-lingual diagnosis system generally includes a prediction module 316 employing a classifier 310 trained using the methods described above with respect to FIG. 2. A display 302 may be, for example, a component of a patient device or a display connected to a device in a clinical setting. Generally, the display 302 presents a prompt to a patient to elicit speech from the patient, such as a picture for the patient to describe or text instruction the patient to tell a story or describe a routine. In some implementations, a physician or other system administrator may vary the prompt given for an individual patient. In other implementations, the system includes a fixed prompt. Where the display 302 is part of a patient device, a microphone (or other recording device) either connected to or integrated in the patient device is used to record and collect patient speech. In some implementations, a video device may be used to collect an alternative to patient speech (e.g., sign language). A microphone communicatively connected to the cross-lingual diagnosis system may also be used to collect and record patient speech in response to the prompt presented on the display 302. A voice to text module 304 converts the recorded speech to a text transcript of the patient speech. The voice to text module 304 may be located on the patient device or may be remote from a patient device. In some implementations, the voice to text module 304 may be replaced with, or in addition to, a video to text module configured to generate transcripts from patients using sign language instead of verbal speech.

The feature extraction module 306 receives the text transcript from the voice to text module 304 and extracts both simple and complex features from the each of a set of speech records. The set of speech records may include, for example, audio recordings of speech and text transcripts of speech. The speech record for one instance of speech may be the combination of a recording of the speech and a text transcript of the speech. In some implementations, the feature extraction module 306 is configured to extract only the features included in the full feature vector used by the classifier 310 in generating a classification. The feature extraction module 306 may also include or connect to additional resources, such as part of speech taggers for languages included in the prediction system, to assist the feature extraction module 306 in calculating and extracting sophisticated features. The feature extraction module 306 generates a feature vector 308 including values for features included in the final feature vector selected in the training stage of the classifier 310.

The feature vector 308 is communicated to a prediction module 316 that includes the trained classifier 310. As shown in FIG. 3, the trained classifier 310 is a random forest classifier, though other classifiers may be used in other implementations. The random forest classifier 310 includes a plurality of individual decision trees 318, 320, 322, and 324 that receive feature subsets 326, 328, 330, and 332, respectively. Generally, a random forest will include hundreds of decision trees. Four are shown in FIG. 3 for simplicity. Each of the decision trees 318, 320, 322, and 324 generate a classification based on their respective feature subsets 326, 328, 330, and 332. The feature subsets 326, 328, 330, and 332 are subsets of the features in the feature vector 308 and are randomly selected for each of the individual decision trees 318, 320, 322, and 324 during training of the classifier 310. The classification 312 of the random forest 310 is based on a consensus of the individual decision trees 318, 320, 322, and 324.

The classification 312 is output to a display 314, which may be the same as the display 302 or may be a display of a physician device, caregiver device, or other computing device. The classification 312 may be output to several computing devices at the same time. For example, the classification 312 may be output to the display 314 of a physician device and simultaneously sent (e.g., via e-mail) to a caregiver device and/or to a patient's electronic medical record. The classification 312 may be accompanied by interpretive information regarding the prediction module 316. For example, where the classification 312 is expressed as a probability of a patient having a neurodegenerative disease, the classification 312 may include a listing of relative weighting of features by the prediction module 316 in determining the probability. Such interpretive information may also include identification of features, how features are grouped or aggregated, or other information providing further explanation regarding functionality of the classifier 310, the prediction module 316 and other components of the system in generating the classification 312. Such interpretive information may, for example, assist physicians in understanding the methodology of the system instead of providing physicians with a "black box" solution.

In some implementations, the classification 312 may be accompanied by a cognitive profile 336, which may include scores for the transcript on features to provide the further context for the classification to a physician, patient, caregiver, or other relevant party. The cognitive profile 336 may be generated by a statistical module 334 receiving the feature vector 308 as input. The statistical module 334 may, for example, aggregate feature scores to generate scores for categories of features and give additional context to the scores based on historical data. For example, some implementations may show the patient's scores relative to various cohorts (e.g., similarly aged patients, patients with Alzheimer's, patients with aphasia, etc.) or display "cutoff scores" for diagnosis or consideration of neurodegenerative diseases. Some implementations may also show how an individual patient's scores have changed over time. The information in the cognitive profile 336 may accordingly be presented with any combination of charts, graphs, tables, or narrative description. In some implementations, the information presented in the cognitive profile 336 may differ depending on whether the cognitive profile 336 is sent to a patient, physician, or other caregiver.

Figure 4:
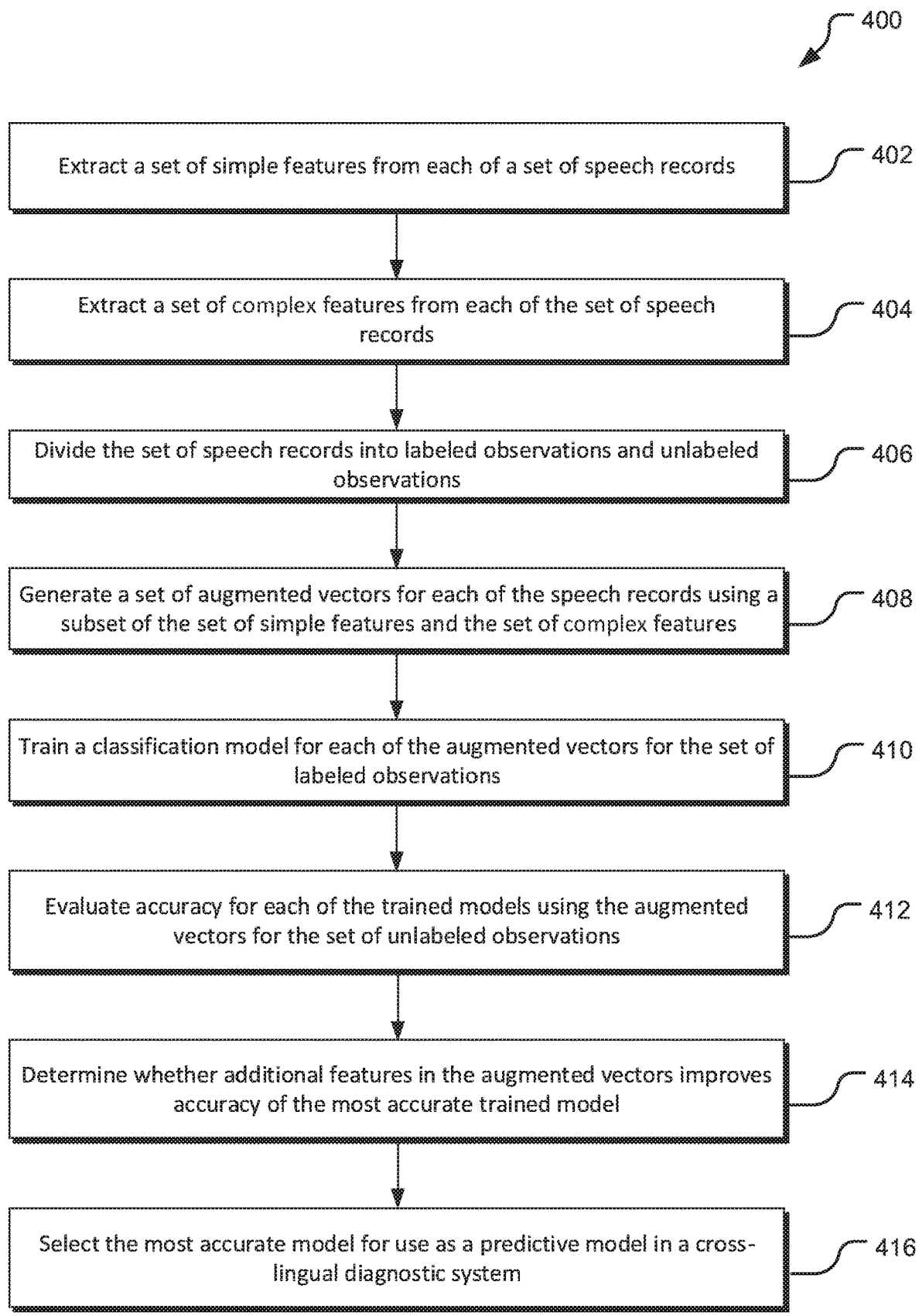
FIG. 4 is a flow diagram for training a prediction model for cross-lingual diagnosis of neurodegenerative disease.

FIG. 4 is a flow diagram of steps 400 for creating a model for prediction of a disease state based on patient speech in multiple languages. A first extracting operation 402 extracts a set of simple features from a set of speech records. The set of speech records generally includes records from healthy patients and from patients having a neurodegenerative disease, where the status of the patients producing the outcomes is known. Further, the subset of speech records includes transcripts, audio recordings, or other records in every language to be included in the prediction system. In some implementations, all speech records in the set are generated in response to the same task (e.g., all are describing the same picture). In other implementations, the speech records may be generated in response to different tasks or from free speech.

Word based features are generally bag of word features (or tf-idf vectors), measuring the number of instances of a specific word or combination of consecutive words in comparison to the total number of words in a transcript or recording. Word based features may be extracted by identifying each individual word used in a set of transcripts in response to a task. In some implementations, words that naturally occur frequently (e.g., "a" or "the") may be removed from the subset of word based features if they are determined (e.g., through inverse document frequency) to be unlikely to be significant in distinguishing between two classes. Additionally, individual words may be lemmatized such that multiple words can be analyzed as a single item. For example, "flower" and "flowers" would be considered the same unigram. Words with identical meanings in each language included in the cross-lingual model may also be considered to be the same unigram.

A second extracting operation 404 extracts a set of complex features from the set of speech records. Complex features generally roughly measure concepts such as lexical complexity and are more complicated to extract from transcripts or audio recordings. Extraction of complex features generally includes analysis of the speech as a whole. For example, features such as various parts of speech ratios, mean length of sentences, and multi verb sentence variation may employ the addition of a speech tagger to identify parts of speech and sentences in each transcript. A feature extraction module (e.g., feature extraction module 204) may have access to speech taggers in multiple languages to pre-process the transcripts before extracting the complex features. Data generated by part-of-speech taggers and syntactic parsers may be used by the feature extraction module in calculating values for complex features.

A dividing operation 406 divides the set of speech records into labeled observations and unlabeled observations. Generally, the dividing operation 406 will randomly divide the set of speech records into labeled observations and unlabeled observations. The records used as labeled observations may be further randomly divided to generate separate training groups for cross-validation of trained models. In some implementations, an additional operation may check the division of the records to ensure that each group includes records from both healthy patients and patients with neurodegenerative disease in each language to be included in the cross-lingual model.

A generating operation 408 generates a set of augmented vectors for each of the records. In some implementations, the augmented vectors each include the set of complex features and a unique one of the set of word based features, such that the final feature vector is guaranteed to include each of the complex features. For example, for a set of records with 300 complex features and 100 word based features, each vector will include 301 features (the entire set of complex features and one of the 100 word based features for a particular transcript and audio recording). In other implementations, FFS is conducted for both the complex features and the word based features, such that the set of augmented vectors is generated iteratively at each iteration of the FFS over the entire set of features.

A training operation 410 trains a classification model for each of the augmented vectors for the set of labeled observations. An evaluating operation 412 evaluates accuracy for each of the trained models using the augmented vectors for the set of unlabeled observations. The trained classification models are utilized to generate a prediction for each of the unlabeled observations. The classification determined by the classification model is then compared to the known classification for each unlabeled observation to calculate accuracy of the classification model. The accuracy may be calculated by averaging or otherwise aggregating the comparisons between the known classifications and the model's prediction. Other performance metrics may also be used to evaluate the classifier's performance, such as sensitivity, specificity and area under the ROC curve.

A determining operation 414 determines whether additional features improve accuracy of the model. Generally, the determining operation 414 selects the most accurate model evaluated during the evaluating operation 412. The method then returns to the generating operation 408 to generate additional augmented vectors for features remaining in the feature vectors that have not yet been included in the most accurate augmented vector. The method continues using the new augmented vectors to train and evaluate a new set of classifiers. The most accurate of the new set of classifiers is then compared to the most accurate classifier in the previous iteration of the method. When the most accurate of the new set of classifiers is more accurate than the most accurate classifier from the previous iteration, the method returns to the generating operation 408 to generate additional augmented vectors. When the most accurate of the new set of classifiers is not more accurate than the most accurate classifier from the previous iteration, additional features no longer improve the accuracy of the model and the method proceeds to a selecting operation 416. The selecting operation 416 selects the most accurate model for use as a predictive model in a prediction system.

Figure 5:
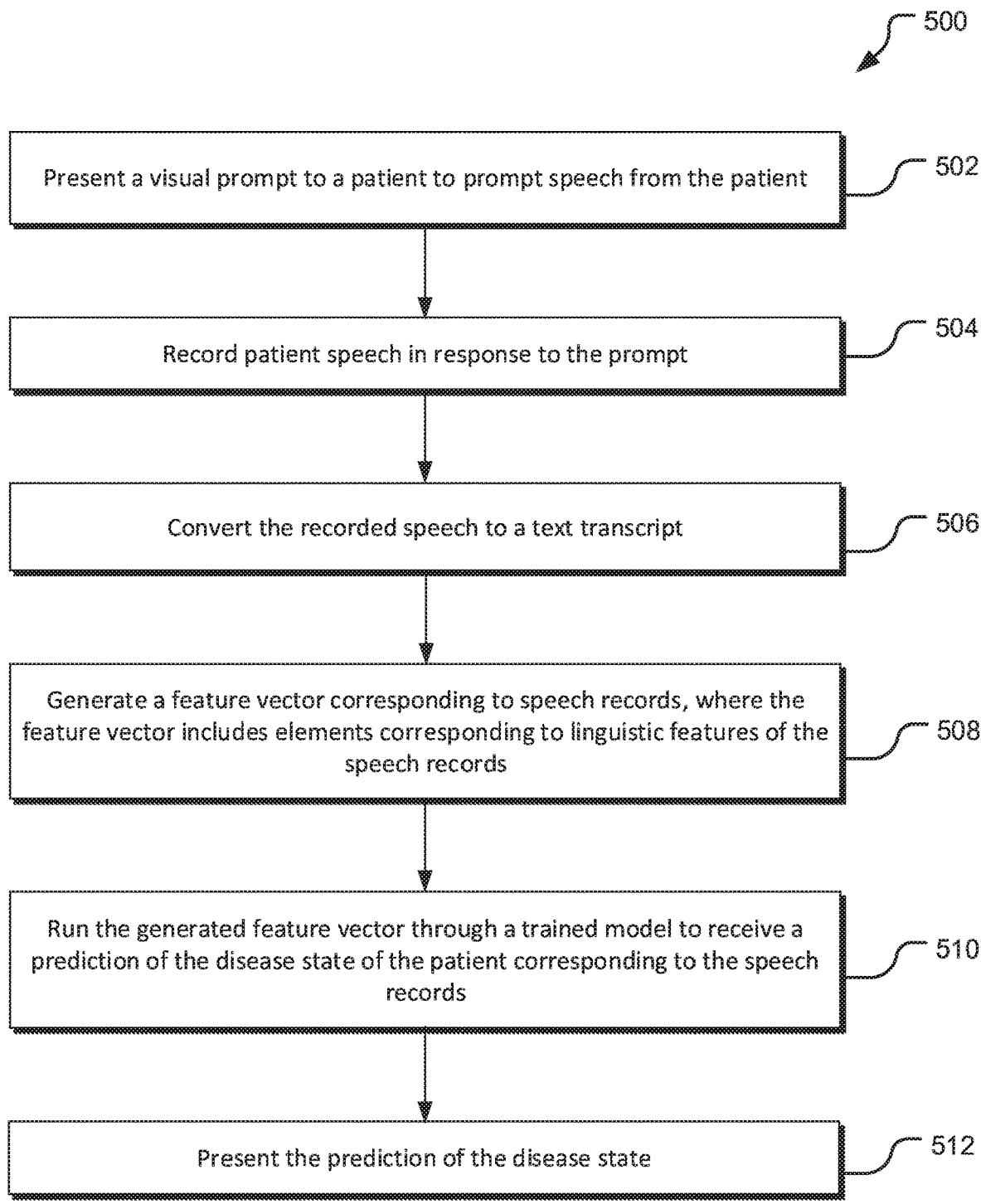
FIG. 5 is a flow diagram of steps for using a diagnosis decision support system to generate a classification for a patient.

FIG. 5 is a flow diagram of steps 500 for generating a prediction of a disease state for a patient based on prompted speech from the patient. A first presenting operation 502 presents a prompt to a patient to prompt speech from the patient. The prompt may be presented as a visual prompt (e.g., via a display on patient device 102) showing a picture with instructions to describe the picture or showing text instructions to the patient. The prompt may also be presented to the patient through, for example audio or tactile outputs of a patient device 102. For example, a patient may receive audio instructions to retell a popular story or to describe a common task. In other implementations, the presenting operation 102 may present a user interface for collecting free form speech from a patient (e.g., recording a conversation). A recording operation 504 records patient speech. The speech may be recorded using a microphone or other speech collection device integrated into or communicatively connected to a patient device 102. In some implementations, the recording operation 504 may include a video recording of a patient using a sign language to communicate instead of speech.

A converting operation 506 converts the recorded speech to a text transcript. The converting operation 506 may occur on a patient device 102 or the patient device 102 may send the recorded speech to a remote processor for conversion to a text transcript. The converting operation 506 may use standard speech-to-text converters for each language included in the prediction system. In some implementations, the speech-to-text converters may be tailored to, for example, a specific dialect of a language to generate more accurate transcripts for patients in a specific geographic region using that dialect. The converting operation 506 generally creates a text file transcript of the recorded speech.

A generating operation 508 generates a feature vector corresponding to the speech record of the speech, which may include both the text transcript and the audio recording. The feature vector includes elements corresponding to linguistic features of the speech records. In cross-lingual models, the linguistic features may be chosen to predict a disease state for speech records in two or more distinct languages. The generating operation 508 may include preprocessing steps such as part of speech tagging to assist in identifying and calculating features of the text transcript. The generating operation 508 outputs a feature vector including a numerical value representative of each feature included in the feature vector.

A running operation 510 runs the generated feature vector through a trained model to receive a prediction of the disease state of the patient corresponding to the speech record. The trained model may be trained to generate predictions for speech records in two or more languages using labeled and unlabeled observations. The trained model may be any type of classifier such as a random forest, naïve Bayes classifier, or decision tree. In some implementations, the type of classifier used may be determined during the training phase by evaluating the accuracy of several different classifiers. The trained model may also be another type of machine learning model such as a deep learning model or a neural network.

A second presenting operation 512 presents the prediction of the disease state. The presenting operation 512 may, in some implementations, present additional information such as scores for particular features, patient performance over time, or a general confidence interval of the trained classifier to help contextualize the prediction. The presenting operation 512 may present the information to the patient (e.g., via patient device 102), to a physician or clinician (e.g., via physician device 114), to caregivers or other interested parties, or to all parties at once. In some implementations, the presenting operation 512 may occur in response to an entry of credentials by the party viewing the disease state prediction to ensure that the party should have access to the information.

Analytics information presented as part of the second presenting operation 512 may include information about how the system generated the prediction. Such analytics may be presented as raw values (raw output from the API) or may be shown using visual aids such as graphs through a UI of, for example, the patient device 102 or the physician device 114. The analytics may explain the model's prediction, including which features contributed most to decisions of the model. Comparisons of average or mean values may be shown between cohorts. Additional descriptive analytics may include comparisons of groups of features based on patient age, education, gender, etc.

Figure 6:
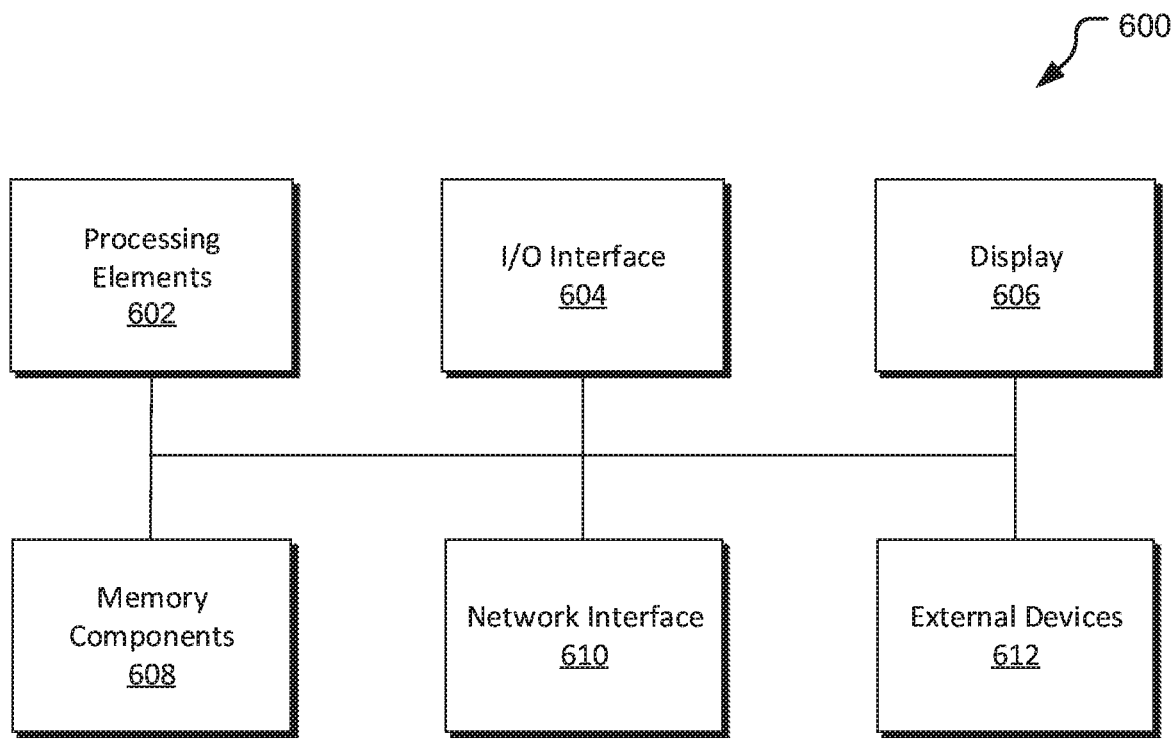
FIG. 6 is a schematic diagram of an example computer system for implementing various embodiments in the examples described herein.

FIG. 6 is a schematic diagram of an example computer system for implementing various embodiments in the examples described herein. A computer system 600 may be used to implement the patient device 102 or the physician device 114 (in FIG. 1) or integrated into one or more components of the prediction system 100. For example, the speech to text module 104, feature extraction module 106, and/or the trained model 110 may include one or more of the components of the computer system 600 shown in FIG. 6. The computer system 600 is used to implement or execute one or more of the components or operations disclosed in FIGS. 1-5. In FIG. 6, the computer system 600 may include one or more processing elements 602, an input/output interface 604, a display 606, one or more memory components 608, a network interface 610, and one or more external devices 612. Each of the various components may be in communication with one another through one or more buses, communication networks, such as wired or wireless networks.

The processing element 602 may be any type of electronic device capable of processing, receiving, and/or transmitting instructions. For example, the processing element 602 may be a central processing unit, microprocessor, processor, or microcontroller. Additionally, it should be noted that some components of the computer 600 may be controlled by a first processor and other components may be controlled by a second processor, where the first and second processors may or may not be in communication with each other.

The memory components 608 are used by the computer 600 to store instructions for the processing element 602, as well as store data, such as speech records, such as speech recordings and/or transcripts (e.g., 202 in FIG. 2), and the like. The memory components 608 may be, for example, magneto-optical storage, read-only memory, random access memory, erasable programmable memory, flash memory, or a combination of one or more types of memory components.

The display 606 provides visual feedback to a user, such as a display of the user device 102 (FIG. 1). Optionally, the display 606 may act as an input element to enable a user to control, manipulate, and calibrate various components of the computational analysis system 100 (FIG. 1) as described in the present disclosure. The display 606 may be a liquid crystal display, plasma display, organic light-emitting diode display, and/or other suitable display. In embodiments where the display 606 is used as an input, the display may include one or more touch or input sensors, such as capacitive touch sensors, a resistive grid, or the like.

The I/O interface 604 allows a user to enter data into the computer 600, as well as provides an input/output for the computer 600 to communicate with other devices or services (e.g., user device 102, physician device 114 and/or other components in FIG. 1). The I/O interface 604 can include one or more input buttons, touch pads, and so on.

The network interface 610 provides communication to and from the computer 600 to other devices. For example, the network interface 610 allows the cross-lingual prediction system to communicate with the user device 102 and the physician device 114 (FIG. 1) through a communication network. The network interface 610 includes one or more communication protocols, such as, but not limited to WiFi, Ethernet, Bluetooth, and so on. The network interface 610 may also include one or more hardwired components, such as a Universal Serial Bus (USB) cable, or the like. The configuration of the network interface 610 depends on the types of communication desired and may be modified to communicate via WiFi, Bluetooth, and so on.

The external devices 612 are one or more devices that can be used to provide various inputs to the computing device 600, e.g., mouse, microphone, keyboard, trackpad, or the like. The external devices 612 may be local or remote and may vary as desired. In some examples, the external devices 612 may also include one or more additional sensors.

The foregoing description has a broad application. For example, while examples disclosed herein may focus on central communication system, it should be appreciated that the concepts disclosed herein may equally apply to other systems, such as a distributed, central or decentralized system, or a cloud system. For example, the speech to text module 104, the feature extraction module 106, the trained model 110, and/or other components in the prediction system 100 (FIG. 1) may reside on a server in a client/server system, on a user mobile device, or on any device on the network and operate in a decentralized manner. One or more components of the prediction system 100 (FIG. 1) may also reside in a controller virtual machine (VM) or a hypervisor in a VM computing environment. Accordingly, the disclosure is meant only to provide examples of various systems and methods and is not intended to suggest that the scope of the disclosure, including the claims, is limited to these examples.

The technology described herein may be implemented as logical operations and/or modules in one or more systems. The logical operations may be implemented as a sequence of processor-implemented steps directed by software programs executing in one or more computer systems and as interconnected machine or circuit modules within one or more computer systems, or as a combination of both. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the procedural operations. One implementation of a computer program product provides a non-transitory computer program storage medium readable by a computer system and encoding a computer program. It should further be understood that the described technology may be employed in special purpose devices independent of a personal computer.

The above specification, examples and data provide a complete description of the structure and use of exemplary embodiments of the invention as defined in the claims. Although various embodiments of the claimed invention have been described above with a certain degree of particularity, or with reference to one or more individual embodiments, it is appreciated that numerous alterations to the disclosed embodiments without departing from the spirit or scope of the claimed invention may be possible. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

The invention claimed is:

1. A method comprising:
   generating a feature vector representing a speech occurrence wherein:

the feature vector comprises a plurality of lingual features of the speech occurrence, and the lingual features are chosen based on accuracy in determining a disease state, and the lingual features include both word based features derived from analysis of words within the speech occurrence and complex features derived from analysis of the speech occurrence as a whole, wherein the lingual features are selected as features being highly predictive of the disease state across two or more languages;

generating a prediction by passing the feature vector as input to a decision module, the decision module comprising a machine learning model trained using data regarding disease state; and returning the prediction to one or more user devices.

2. The method of claim 1, wherein the word based features include at least one unigram feature indicating a recurrence of a word in the speech.

3. The method of claim 1, wherein the complex features include at least one acoustic feature extracted from an audio recording of the speech.

4. The method of claim 1, wherein returning the prediction to the one or more user devices comprises returning context information with the prediction.

5. The method of claim 4, wherein the context information includes at least one of the lingual features of the speech occurrence and patient performance history.

6. The method of claim 1, wherein the feature vector is generated by extracting one or more of the lingual features from an audio recording of the speech and extracting one or more of the lingual features from a transcript of the speech.

7. The method of claim 1, wherein the speech occurrence is a first language and the machine learning model is trained using data in a second language.

8. The method of claim 1, wherein the complex features comprise one or more of lexical complexity, mean sentence length, word repetition, a variety of words, inflection, semantic coherence, or cohesion specificity.

9. The method of claim 1, wherein the lingual features are extracted from data sets comprising multiple languages.

10. The method of claim 1, wherein the lingual features are determined based in part by a forward feature selection or a recursive feature elimination.

11. The method of claim 1, wherein the machine learning model is trained using data generated in response to speech captured in response to two or more different tasks and in two or more languages.

12. A method comprising:

extracting features of speech from one or more datasets including speech records in a first language and speech records in a second language, wherein the one or more datasets include speech records and a known outcome corresponding to each of the speech records; and identifying a subset of the extracted features for accurately predicting a disease state or risk factor for speech records in both the first language and the second language by:

training a plurality of models using different experimental subsets of features to predict the disease state for each of the speech records, assessing an accuracy of the plurality of models by comparing the predicted disease state to the known outcome for each of the speech records, and identifying the experimental subset of features used to train one or more models based on the assessed accuracy.

13. The method of claim 12, wherein the extracted features include both word based features derived from analysis of words within the speech and complex features derived from analysis of the speech as a whole.

14. The method of claim 13, wherein each of the experimental subsets of features includes at least one unique word based feature of the word based features.

15. The method of claim 12, wherein identifying the experimental subset of features used to train one or more models based on the assessed accuracy comprises:

identifying a most accurate model of the plurality of models based on the assessed accuracy of the plurality of models; and designating the experimental subset of features used to train the most accurate model as the subset of features for accurately determining a disease state for transcripts in both the first language and the second language.

16. The method of claim 12, further comprising:

configuring a system for cross-lingual diagnosis by:

identifying a most accurate model of the plurality of models based on the assessed accuracy of the plurality of models;

configuring a second feature extraction module to extract the experimental subset of features used to train the most accurate model from speech records in the first language and the second language; and configuring a prediction module including the most accurate model.

17. The method of claim 12, wherein the speech records include recorded audio of speech and written transcripts of speech.

18. The method of claim 12, wherein the plurality of models are random forest classifiers.

19. The method of claim 12, wherein the speech records are free form speech.

20. A system for predicting a disease state based on a speech occurrence, the system comprising:

a feature extraction module configured to extract a plurality of lingual features from speech of the speech occurrence, wherein the plurality of lingual features are experimentally determined to have a high predictive value of the disease state for speech in each of a first language and a second language and include both word based features and complex features, wherein word based features comprise features derived from analysis of words within the speech, and complex features comprise features derived from analysis of the speech as a whole;

a prediction module including a trained classification model, wherein the trained classification model is trained to generate a prediction of the disease state for a patient based on the speech using the plurality of lingual features extracted from the speech; and a communication interface configured to return the prediction of the disease state and one or more analytics regarding the speech and the lingual features to a user device for display to a user.

21. The system of claim 20, wherein the word based features include one or more unigram features indicating a recurrence of a word in the speech.

22. The system of claim 20, wherein experimentally determining high predictive value of the plurality of lingual features occurs while training the trained classification model.

23. The system of claim 20, wherein the complex features include at least one acoustic feature extracted from an audio recording of the speech.

24. The system of claim 23, wherein the analytics returned by the communication interface include patient scores in predetermined linguistic categories, wherein the plurality of lingual features correlate to one of the predetermined linguistic categories.

25. The system of claim 23, wherein the communication interface is further configured to receive a final diagnosis from a user device, wherein the final diagnosis is communicated to the prediction module to refine the trained classification model.

* * * * *